(12) United States Patent
Wachinger

(10) Patent No.: US 10,473,631 B2
(45) Date of Patent: Nov. 12, 2019

(54) SAMPLER FOR LIQUID CHROMATOGRAPHY

(71) Applicant: DIONEX SOFTRON GMBH, Germering (DE)

(72) Inventor: Thomas Wachinger, Altomuenster (DE)

(73) Assignee: Dionex Softron GMBH, Germering (DE)

( * ) Notice: Subject to any disclaimer, the term of this patent is extended or adjusted under 35 U.S.C. 154(b) by 99 days.

(21) Appl. No.: 15/190,529

(22) Filed: Jun. 23, 2016

(65) Prior Publication Data

US 2016/0377580 A1    Dec. 29, 2016

(30) Foreign Application Priority Data

Jun. 25, 2015  (DE) ................ 10 2015 110 254

(51) Int. Cl.
*G01N 30/20* (2006.01)
*G01N 30/24* (2006.01)

(52) U.S. Cl.
CPC ............ *G01N 30/20* (2013.01); *G01N 30/24* (2013.01); *G01N 2030/201* (2013.01); *G01N 2030/202* (2013.01)

(58) Field of Classification Search
CPC ..................................................... G01N 30/20
See application file for complete search history.

(56) References Cited

U.S. PATENT DOCUMENTS

| | | |
|---|---|---|
| 1,577,012 A | 3/1926 | Crane |
| 3,530,721 A | 9/1970 | Hrdina |
| 4,068,528 A | 1/1978 | Gundelfinger |
| 4,182,184 A | 1/1980 | Bakalyar et al. |
| 4,300,393 A | 11/1981 | Stearns |
| 4,444,066 A | 4/1984 | Ogle et al. |
| 4,506,558 A | 3/1985 | Bakalyar |
| 4,883,409 A | 11/1989 | Strohmeier et al. |
| 4,939,943 A | 7/1990 | Strohmeier |

(Continued)

FOREIGN PATENT DOCUMENTS

| | | |
|---|---|---|
| CN | 1327157 | 12/2001 |
| DE | 3223852 A1 | 1/1983 |

(Continued)

OTHER PUBLICATIONS

Fujinari, "New Alternative to Normal Phase HPLC Automation Using Methylene Chloride Mobile Phases: A Synchronized Dual Switching Valve Loop injection System," Journal of High Resolution Chromatography & Chromatography Communications, Aug. 1988, pp. 595-598, No. 8, Heidelberg, W. Germany (4 pages).

(Continued)

*Primary Examiner* — Lisa M Caputo
*Assistant Examiner* — Alex T Devito
(74) *Attorney, Agent, or Firm* — Timothy J. Ohara

(57) ABSTRACT

A sampler for liquid chromatography is described. The sampler includes an injection valve and a sample loop. The injection valve includes one waste port, two sample loop ports, and two high-pressure ports. The sample loop port includes a first loop part and a second loop part. The injection valve can be configured to have LOAD position and INJECT position. The injection valve can also be configured to have one or more additional positions such as a FULL PURGE position, a PUMP PURGE position, and a NEGATIVE PRESSURE position.

29 Claims, 4 Drawing Sheets

(56) References Cited

U.S. PATENT DOCUMENTS

| | | | |
|---|---|---|---|
| 5,105,851 A | 4/1992 | Fogelman |
| 5,108,264 A | 4/1992 | Abdel-Rahman |
| 5,207,109 A | 5/1993 | Olsen |
| 5,637,208 A | 6/1997 | Dourdeville |
| 5,730,943 A | 3/1998 | Ford et al. |
| 5,803,117 A | 9/1998 | Olsen et al. |
| 6,012,487 A | 1/2000 | Hauck |
| 6,129,840 A | 10/2000 | Kitaoka |
| 6,155,123 A | 12/2000 | Bakalyar |
| 6,260,407 B1 | 7/2001 | Petro et al. |
| 6,281,019 B1 | 8/2001 | Werringloer |
| 6,382,035 B1 | 5/2002 | Nichols |
| 6,416,663 B1 | 7/2002 | Miroslav et al. |
| 6,428,702 B1 | 8/2002 | Berger et al. |
| 6,475,391 B2 | 11/2002 | Safir et al. |
| 6,485,642 B2 | 11/2002 | Kaito et al. |
| 6,874,354 B2 | 4/2005 | Cueni et al. |
| 6,976,383 B2 | 12/2005 | Petro et al. |
| 7,377,291 B2 | 5/2008 | Moon et al. |
| 7,503,203 B2 | 3/2009 | Gamache et al. |
| 7,588,725 B2 | 9/2009 | Ozbal et al. |
| 8,196,456 B2 | 6/2012 | Hochgraeber et al. |
| 8,312,762 B2 | 11/2012 | Fadgen et al. |
| 8,806,922 B2 | 8/2014 | Hochgraeber |
| 8,921,113 B2 | 12/2014 | Lin et al. |
| 9,086,426 B2 | 7/2015 | Liu et al. |
| 9,435,773 B2 | 9/2016 | Glatz et al. |
| 10,031,112 B2 | 7/2018 | Hochgraeber |
| 2002/0008058 A1 | 1/2002 | Nugent |
| 2003/0098076 A1 | 5/2003 | Nichols |
| 2005/0061722 A1 | 3/2005 | Takao et al. |
| 2005/0194318 A1 | 9/2005 | Ozbal et al. |
| 2006/0042686 A1 | 3/2006 | Gamache et al. |
| 2006/0191581 A1 | 8/2006 | Cueni et al. |
| 2006/0219618 A1 | 10/2006 | Witt et al. |
| 2006/0260700 A1 | 11/2006 | Bauerle et al. |
| 2007/0251302 A1 | 11/2007 | Iwata |
| 2008/0022765 A1 | 1/2008 | Witt et al. |
| 2008/0047611 A1 | 2/2008 | Stemer |
| 2009/0144520 A1 | 6/2009 | Hochgraeber et al. |
| 2009/0145205 A1 | 6/2009 | Hochgraeber et al. |
| 2010/0260617 A1 | 10/2010 | Haertl |
| 2010/0288025 A1 | 11/2010 | Hochgraeber |
| 2012/0132013 A1 | 5/2012 | Glatz et al. |
| 2013/0067997 A1 | 3/2013 | Ebsen et al. |
| 2014/0007660 A1 | 1/2014 | Moeller et al. |
| 2014/0197247 A1 | 7/2014 | Stearns et al. |
| 2014/0338431 A1 | 11/2014 | Hochgraeber |
| 2014/0345371 A1 | 11/2014 | Hochgraeber |
| 2014/0345372 A1 | 11/2014 | Gerhardt et al. |
| 2015/0265944 A1 | 9/2015 | Hochgraeber et al. |

FOREIGN PATENT DOCUMENTS

| | | |
|---|---|---|
| DE | 19628206 A1 | 1/1998 |
| DE | 10222334 A1 | 12/2003 |
| DE | 102004052584 A1 | 1/2006 |
| DE | 112005000128 T5 | 5/2007 |
| DE | 102007059651 A1 | 6/2009 |
| DE | 102008006266 A1 | 8/2009 |
| DE | 102013215065 A1 | 2/2015 |
| EP | 0244751 A2 | 11/1987 |
| EP | 0321774 A2 | 6/1989 |
| EP | 0327658 A1 | 8/1989 |
| EP | 1536228 A1 | 6/2005 |
| EP | 1577012 A1 | 9/2005 |
| EP | 1879026 A1 | 1/2008 |
| EP | 2051071 A1 | 4/2009 |
| EP | 2196801 A1 | 6/2010 |
| JP | 54089692 A | 7/1979 |
| JP | S60143279 A | 7/1985 |
| JP | 62272155 A | 11/1987 |
| JP | 05307026 A | 11/1993 |
| JP | 07072130 A | 3/1995 |
| JP | H08159310 A | 6/1996 |
| JP | 3491948 B2 | 2/2004 |
| JP | 2006058146 A | 3/2006 |
| JP | 2007327845 A | 12/2007 |
| JP | 2007327846 A | 12/2007 |
| JP | 2008051746 A | 3/2008 |
| JP | 2008529010 A | 7/2008 |
| JP | 2009053098 A | 3/2009 |
| WO | WO-0239105 A1 | 5/2002 |
| WO | WO2004025272 A1 | 3/2004 |
| WO | 2006023828 A2 | 3/2006 |
| WO | WO2006083776 A2 | 8/2006 |
| WO | WO2006089389 A8 | 10/2006 |
| WO | 2007109529 A2 | 9/2007 |
| WO | 2008005845 A2 | 1/2008 |
| WO | WO2008103098 A1 | 8/2008 |
| WO | WO-2009003520 A1 | 1/2009 |
| WO | WO2009092345 A1 | 7/2009 |
| WO | 2009108219 A2 | 9/2009 |
| WO | 2009108219 A3 | 9/2009 |
| WO | 2010139359 A1 | 12/2010 |
| WO | WO-2014199198 A1 | 12/2014 |

OTHER PUBLICATIONS

Agilent Technologies, Inc.; Agilent 1100 Series HPLC Value System; pp. 1-76, 1999.
Agilent Technologies; Agilent 1200 Series HPLC-Chip/MS System; pp. 1-8; Aug. 1, 2008.
Angelika Gratzfeld-Fluesgen et al., Agilent 1200 Series Rapid Resolution LC and Rapid Resolution LD/MS Optimization Guide; Agilent Technologies; pp. 1-133, Jan. 2009.
Eieinhauer et al., "Bulk derivatization and cation exchange restricted access media-based trap-and-elute liquid chromatography-mass spectrometry method for determination of trace estrogens in serum," Analytica Chimica Acta, 858, 74-81, 2015.
Brotto, Jun. 15, 2017, manuscript No. ACA-17-727, 95 pgs.
Canadian Office Action issued in CA app. No. 2,764,047, dated Jul. 10, 2015, 6 pgs.
Chinese-language Office Action (with English translation) issued in CN app. No. 200980159715.9 dated Oct. 15, 2013, 25 pgs.
COSMOS program for Aug. 17-19, 2015 Conference, http://www.cosmoscience.org/blog/archives/2015-cosmos/2015-agenda/ accessed Jun. 21, 2017, 18 pgs.
EP Communication pursuant to Article 94(3) EPC issued in EP app. No. 09779619.7 dated Jun. 27, 2013, 4 pgs.
EP Communication pursuant to Article 94(3) EPC issued in EP app. No. 09779619.7 dated Oct. 18, 2012, 6 pgs.
Excerpt from VICI AG Valco Cheminert Catalog (1999), 17 pgs.
Excerpt from VICI Valco Cheminert Catalog (2005), 27 pgs.
Fan and Schug, "Hyphenation of Flow-Injection Analysis with Mass Spectrometry: A Versatile and High-Throughput Technique," Current Trends in Mass Spectrometry, May 2012, 6 pgs.
Fan et al., "Bulk-derivatization and direct injection of human cerebrospinal fluid for trace-level quantification of endogenous estrogens using trap-and-elute liquid chromatography with tandem mass spectroscopy," J. Sep. Sci., 37, 2010-2017, 2014.
Final Office Action issued in U.S. Appl. No. 13/375,884, dated Mar. 1, 2016, 11 pgs.
Final Office Action issued in U.S. Appl. No. 14/877,758, dated Jun. 14, 2016, 15 pgs.
International Search Report and Written Opinion issued in PCT/EP2009/056795, dated Jan. 13, 2010, 16 pgs.
Japanese-language Office Action issued in JP app. No. 2012-513477, dated Oct. 11, 2013 (with English translation), 6 pgs.
Kevin A. Schug, Ph.D., slide presentation for Aug. 17-19, 2015 Conference on Small Molecule Science, 32 pgs.
Kevin Schug, Ph.D., Chemistry Spring 2017 course syllabus for Instrumental Analysis, 30 pgs.
Kretz et al., "Automatic Liquid Chromatography Injection and Sampling," Hewlett-Packard Journal, Apr. 1984, 4 pgs.
Non-final Office Action issued in U.S. Appl. No. 14/877,758, dated Mar. 2, 2016, 19 pgs.
Notice of Allowance issued in U.S. Appl. No. 13/375,884, dated May 10, 2016, 11 pgs.

(56) References Cited

OTHER PUBLICATIONS

Papouskova et al., "Aspects of trapping efficiency and matrix effects in the development of a restricted-access-media-based trap-and-elute liquid chromatograhy with mass spectrometry method," J. Sep. Sci., 37, 2192-2199, 2014.

Preliminary amendment submitted in U.S. Appl. No. 13/375,884, filed Feb. 15, 2012, 10 pgs.

Priority document (translation from original German) submitted by Dionex on Jul. 21, 2010 to satisfy 35 U.S.C. 371(c) for National Stage Entry into US of PCT/DE2009/000004, 35 pgs.

U.S. Office Action issued in U.S. Appl. No. 13/375,884, dated Nov. 24, 2015, 17 pgs.

Yang et al., "Quantitative Determination of Bisphenol a From Human Saliva Using Bulk Derivatization and Trap-and-Elute Liquid Chromatography Coupled to Electrospray Ionization Mass Spectrometry," Environmental Toxicology and chemistry, 30(6), 2011, 1243-1251.

Yang et al., "Restricted access media as a streamlined approach toward on-line sample preparation: Recent advancements and applications," J. Sep. Sci. 36, 2922-2938, 2013.

International Search Report and Written Opinion for Application No. PCT/DE2009/00004, dated May 11, 2009, 11 pages.

Opposition filed by Agilent hereby filing an Opposition to German Patent 10 2016 101 658B2, English translation, dated Jan. 4, 2019.

SAMPLER FOR LIQUID CHROMATOGRAPHY

CROSS REFERENCE TO RELATED APPLICATIONS

This application is claims the priority benefit under 35 U.S.C. § 119 to German Patent Application No. DE 10 2015 110 254.4, filed on Jun. 25, 2015, the disclosure of which is incorporated herein by reference.

FIELD OF INVENTION

The present invention relates to a sampler for liquid chromatography, in particular for high performance liquid chromatography (HPLC), which sampler has an injection valve with an extremely low leakage rate and also permits the cleaning of the ports and of the grooves of the injection valve, of the sample loop, of the sample delivery device, of the injection needle and of the needle seat exclusively by way of the solvent pump(s).

BACKGROUND

In HPLC, a sample to be examined must be fed into a high-pressure liquid flow, wherein the latter must be interrupted only for as short a period of time as possible. For this purpose, high-pressure injection valves are used which permit a virtually interruption-free switch of the liquid flow. Such a design is described for example in U.S. Pat. No. 3,530,721 A.

Injection valves used at present have at least four ports in order to permit sample pre-compression by way of a sample delivery device. An additional port is required if it is sought to dispose of solvent contained in the sample delivery device, or of an incorrectly taken-in sample, via a waste port (disposal port) connected to the injection valve. A sampler having a corresponding injection valve is already described in DE 10 2008 006 266 A1.

During a change of the solvent in an HPLC system, it is necessary for old solvent in the lines between the solvent bottles and the injection valve to likewise be flushed out via the waste port. Here, it is for example possible for the so-called injection needle to be moved directly over a waste container and for the contents of the line to be disposed of by way of the solvent pump(s). The disposal is generally referred to as "purge". The abovementioned solvent change is described for example in U.S. Pat. No. 6,129,840 A.

If it is however sought to clean not only the sample delivery device but also the so-called needle seat, use is made, in known solutions, of a second solvent pump for cleaning purposes, as described for example in US 2013067997 A1.

In the prior art, therefore, only the lines from the solvent drawing-in lines to the switching valve, including the sample delivery device and the injection needle, but not the needle seat itself, are flushed through by means of the solvent pump(s). A further cleaning pump is consequently required for this purpose. Owing to the further pump, the construction becomes more complex and more expensive. If a further pump is omitted, contaminants in the needle seat must be accepted, which result in a so-called carry-over between the individually analyzed samples.

In the prior art, for the realization of the sample precompression and sample decompression, for the taking-in of the sample, for the sample injection and for the so-called purging, at least 3 grooves are provided in the stator or in the rotor of the injection valve in order to make it possible for corresponding switching positions to be realized. This has the result that the sealing surface between the connections becomes very small, leading to certain leakage rates. It would accordingly be advantageous to provide an injection valve which, by means of at most 2 grooves, makes it possible to realize all of the required switching states.

Furthermore, in the so-called injection position (INJECT position) of the injection valve, that is to say the position while the sample is transferred to the chromatography column, some connecting lines of a sampler are not fully flushed through. Most connections, formed in the manner of grooves in the stator or rotor of the injection valve, are required in order to be able to switch back and forth between the so-called loading position (LOAD position; introduction of the sample into a sample loop of the injection valve) and the pressure equalization position (PRESSURE EQUALIZATION position; position in which the sample loop is brought to the system pressure or ambient pressure), and also between the INJECT position and the PRESSURE EQUALIZATION position, without the solvent flow to the column being interrupted. The flow must not be interrupted because, otherwise, the pump pressure would rise to an extreme extent and the column pressure would drop. The former is a problem for safety reasons, and in the case of the latter, long equilibration phases are required between the sample analyses. The solvent used at the start of the chromatography run (for example in the equilibration phase) accumulates in said grooves and falsifies the gradient composition during the further process owing to the mixing of the solvent residue with the gradient (which is critical in particular in the case of low-flow/nano-flow applications).

SUMMARY

It is therefore the object of the present invention to provide an injection valve of a sampler, which injection valve is of simple construction, makes do with a small number of ports and grooves connecting the ports, has no cleaning pump, exhibits a more intense sealing action, and has no regions that are not flushed through, and which can furthermore be produced inexpensively, wherein different switching positions of the injection valve should be made possible, such as pressure equalization position, position for receiving the sample, positions for sample injection and for purging the lines from the solvent bottles to the switching valve, with or without sample delivery device, and needle and needle seat, and also a position for producing a negative pressure.

The invention achieves the stated object through the provision of a sampler for liquid chromatography, in particular high performance liquid chromatography, (a) having an actuable injection valve which has at least one waste port for the discharge of fluid at low pressure, a first and a second sample loop port, and two high-pressure ports for the supply and discharge of fluid at high pressure, one high-pressure port being connectable to a pump and the other high-pressure port being connectable to a chromatography column, (b) having a sample loop, (i) which sample loop comprises a first sample loop part which is connected at one end to the first sample loop port and at the other end to a pump volume of a sample delivery device, (ii) which sample loop comprises a second sample loop part which is connected at one end to the second sample loop port and at the other end to the pump volume of the sample delivery device, (iii) the second sample loop part being formed such that it can be divided into a drawing-in part and a supply part, and (iv) it being possible, in the divided state, for a sample fluid to be drawn in by means of the free end of the drawing-in part connected to the pump volume, which sample fluid can, in the connected state, be supplied via the supply part in the direction of the first sample loop port, and (c) the injection valve being designed (i) such that, in a LOAD position, the two high-pressure ports are connected to one another, and that sample loop port which is connected to the second sample loop part is connected to the waste port, and (ii) such that, in an INJECT position, that high-pressure port which is connectable to the pump is connected to the second sample loop port, and that high-pressure port which is connectable to the chromatography column is connected to the first sample loop port, wherein (d1) the injection valve has a FULL PURGE position, in which the second sample loop port is connected to the waste port, and that high-pressure port which is connected to the pump is connected to the first sample loop port, and/or (d2) the injection valve has a PUMP PURGE position in which the second sample loop port is connected to that high-pressure port which is connectable to the chromatography column, and that high-pressure port which is connectable to the pump is connected to the waste port, and/or (d3) the injection valve has a NEGATIVE PRESSURE position in which that high-pressure port which is connectable to the pump is connected to the first sample loop port, and the second sample loop port is sealingly closed.

The feature (d1) has the advantage that both the sample loop and the high-pressure port connected to the pump, the two sample loop ports, the waste port and the sample delivery device can be flushed through by way of the solvent pump (hereinafter referred to merely as "pump"), without it being necessary for the sampler to have a further cleaning pump. The feature (d2) has the advantage that the injection valve can also have a position in which the port connected to the high-pressure pump and the waste port can be flushed through. In the PUMP PURGE position, that sample loop port which is connected to the second sample loop part is preferably sealingly closed off. According to the invention, therefore, the expression FULL PURGE is to be understood to mean a state in which all of the grooves and ports of the injection valve (with the exception of that high-pressure port which is connectable to the chromatography column) and all of the supply and discharge lines, sample loops and the sample delivery device can be flushed through with solvent, and thereby cleaned, preferably by way of a pump. Furthermore, in the FULL PURGE position of the injection valve, it is also possible for the sample needle, from the outside, and the injection port to be washed. For this purpose, the sample needle is moved away from the needle seat (also referred to as injection port) slightly in order that the solvent delivered by the pump washes away contaminants on the outer side of the sample needle and on the needle seat. The contaminated solvent can then flow, for example via an overflow on the needle seat, into a waste vessel. According to the invention, the expression PUMP PURGE is to be understood to mean a state in which the supply line from the pump to the high-pressure port connected thereto, said high-pressure port itself, the connecting groove between said high-pressure port and the waste port, and the waste port itself can be flushed through with solvent and thereby cleaned, and also, solvent can be disposed of. The feature (d3) has the advantage that, in said position, it is possible for a negative pressure to be produced in the sample loop 51, 44, 52 and as far as the pump. Said negative pressure can be produced by virtue of the pump volume of the sample delivery device being increased, preferably by virtue of a movable element (piston) of the sample delivery device being moved outward. The production of the negative pressure makes it possible for the pump to assist in the drawing-in of the solvent, by virtue of the hydrostatic column of the solvent in the solvent bottles being overcome. Furthermore, the NEGATIVE PRESSURE position makes it possible for undesired gas bubbles in the device to be increased in size, such that they can be more easily removed from said device.

A further advantage of the valve construction of the sampler according to the invention lies in the fact that, depending on the switching position of the injection valve, it is possible for virtually all of the provided parts to be flushed through by way of the solvent pump(s). It is thus furthermore preferable for the sampler according to the invention to have at most one (solvent) pump path. Here, the pump path is to be understood to mean the connecting line from the solvent pump(s) to the corresponding high-pressure port. The sampler according to the invention may thus comprise not only one solvent pump but even two or more solvent pumps, which can all supply solvent via the corresponding high-pressure port. According to the invention, it is preferable if the sampler has no further cleaning pump in addition to the one or more solvent pump(s), because, owing to the different switching positions of the injection valve, the cleaning can be performed by way of solvent delivered by the one or more solvent pump(s).

In a further preferred embodiment of the invention, the injection valve of the sampler according to the invention may also, as possible settings, have the FULL PURGE position and the PUMP PURGE position, or the FULL PURGE position and the NEGATIVE PRESSURE position, or the PUMP PURGE position and the NEGATIVE PRESSURE position, or all three positions together.

In a further embodiment of the sampler according to the invention, that high-pressure port to which the column is connected is sealingly closed when the injection valve is in the FULL PURGE position. The same applies to the first sample loop port in the PUMP PURGE position and to the second sample loop port in the NEGATIVE PRESSURE position.

In a further embodiment of the sampler according to the invention, the injection valve has a PRESSURE EQUALIZATION position, in which the first and the second sample loop ports of the closed sample loop do not have a connection to the other ports, that is to say to the two high-pressure ports and to the waste port of the injection valve. Here, it is furthermore preferable if, in the PRESSURE EQUALIZATION position, the two high-pressure ports are connected to one another.

It is furthermore preferable if the injection valve of the sampler according to the invention has at most 5 ports, specifically the two sample loop ports, the two high-pressure ports and the waste port. The reduction to a maximum of 5 ports simplifies the construction of the sampler and reduces the leakage rate in relation to an injection valve with 6 or more ports.

It is furthermore preferable according to the invention if that high-pressure port which is connected to the pump(s) is spaced apart from the two sample loop ports, from the waste port, and from that high-pressure port which is connected to the chromatography column, by in each case substantially the same distance. The expression "substantially" is intended to clarify that, here, merely machining-induced differences in spacing may exist, which however do not influence the functionality of the injection valve. It is furthermore also preferable if the sample loop ports are situated on opposite sides with respect to that high-pressure port which is connected to the pump(s), and the two sample loop ports are spaced apart from the waste port, and from that high-pressure port which is connected to the chromatography column, by in each case substantially the same distance. In this case, too, the expression "substantially" is intended to have the meaning as given above.

Said spacings of the various ports in the two abovementioned preferred embodiments run within a direction of extent of the contact surface of a rotor and of a stator of the injection valve.

Thus, in a further embodiment of the sampler according to the invention, it is preferable if the injection valve has a rotor and a stator, the rotor having a face surface which interacts with the face surface of the stator (contact surface of stator and rotor) and in which there are formed (at least) two grooves by means of which, in a manner dependent on the rotational position of the rotor relative to the stator, port opening cross sections of the two high-pressure ports, of the two sample loop ports and of the waste port provided in the face surface of the stator are connected in pressure-tight fashion or are shut off in pressure-tight fashion. It is furthermore preferable for one groove of the (at least) two grooves, which groove connects the two high-pressure ports in the LOAD position of the injection valve, to be designed such that it still connects the high-pressure ports even after a rotation of the stator relative to the rotor into the PRESSURE EQUALIZATION position.

It is possible according to the invention for the injection valve to also have more than two grooves. However, according to the invention, it is particularly preferable for the injection valve to have at most the two stated grooves, in particular in order to realize all of the stated positions of the injection valve. The number of at most two grooves has the advantage that the leakage rate in the injection valve can be kept very low.

One of the grooves, said groove connecting the two high-pressure ports when the injection valve is in the LOAD position, is preferably of hook-shaped form, and the other of the grooves, said groove connecting the first sample loop port to the waste port when the injection valve is in the LOAD position, is preferably of arcuate form. The two grooves preferably run in the direction of the interacting face surfaces of the rotor and of the stator. The expression "arcuate" is to be understood to mean that the profile of said groove runs over a circular segment around, as a central point, that high-pressure port which is connected to the pump(s). The so-called hook-shaped groove is preferably formed such that, as a result of rotation of the stator and of the rotor relative to one another during a change from the LOAD position into the PRESSURE EQUALIZATION position, a partial extent of the hook permits a connection of said groove to that high-pressure port which is connected to the chromatography column.

Said designs of the grooves and ports in the injection valve of the sampler according to the invention have the advantage that, in virtually all switching positions (with the exception of PRESSURE EQUALIZATION position and NEGATIVE PRESSURE position), all parts of the grooves and ports can be flushed through. In other words, there is virtually no region in the injection valve which cannot be flushed through, such that good cleaning is possible, and no contamination-induced changes in operational behavior occur during HPLC operation.

It is furthermore preferable according to the invention if the injection valve has, at most, the stated six positions, specifically the LOAD position, the PRESSURE EQUALIZATION position, the INJECT position, the PUMP PURGE position, the FULL PURGE position and the NEGATIVE PRESSURE position, preferably in order to be able to realize all required states in a sampler for HPLC. According to the invention, all of the stated positions can be realized by way of the two abovementioned grooves in the injection valve.

The injection valve of the sampler according to the invention is preferably constructed such that, by rotation, it can be transferred into the following positions in the stated sequence: LOAD position→PRESSURE EQUALIZATION position→INJECT position→PUMP PURGE position→FULL PURGE position→NEGATIVE PRESSURE position→LOAD position. This has the advantage that the transitions from the respective switching position into the respectively required subsequent switching position are possible directly and without undesired intermediate switching positions. In this way, there are no sample losses, no undesired mixing with any residues in ports that would otherwise come into contact owing to intermediate switching positions, and no undesired pressure drop.

Furthermore, the sampler according to the invention preferably has a control unit for controlling the injection valve and the sample delivery device.

The sample delivery device may preferably also have a movable element which is guided in sealed fashion in a pump volume and which can be moved by way of a drive, which can be actuated by the control unit, of the sample delivery device for the purposes of delivering the sample fluid contained in the pump volume.

The sample delivery device is preferably of high-pressure-resistant form and can generate pressures which are used in high performance liquid chromatography, preferably pressures of greater than 500 to 600 bar, most preferably pressures of greater than 1500 bar.

The sampler according to the invention has the advantage that the integration of a sample delivery device into the split loop arrangement makes it possible to realize pressure equalization by way of the sample delivery device during the change of switching positions of the injection valve if the injection valve has, for this purpose, a PRESSURE EQUALIZATION position in which those sample loop ports of the injection valve which are connected to the ends of the sample loop are not connected in the injection valve to other ports.

In the case of the split loop principle, the sample loop is divided in the connecting part between the sample delivery device, which may for example be in the form of a syringe, and the respective sample loop port of the injection valve. The end of the drawing-in part, connected to the sample delivery device, of the divided connecting part of the sample loop is, for the purposes of drawing in the required sample volume or drawing in a flushing medium, moved to a sample vessel or to a vessel for the flushing medium. Subsequently, the divided connecting part of the sample loop is connected again, such that the drawn in sample volume can, in the INJECT position of the injection valve, be injected into the chromatography column by means of the pump(s). This basic principle has already been described in U.S. Pat. No. 4,939,943 A1.

According to the invention, the injection valve is, after the drawing-in of the volume in the LOAD position, switched into the PRESSURE EQUALIZATION position in which the sample loop ports are shut off in pressure-tight fashion. In the PRESSURE EQUALIZATION position, the drive of the sample delivery device is preferably actuated such that, in the closed sample loop and in the pump volume of the pump delivery device, a pressure builds up which substantially corresponds to the system pressure. Even if the pressure in the sample loop before the switching of the injection valve from the PRESSURE EQUALIZATION position into the INJECT position is not identical to the system pressure of the pump(s), but a slight pressure difference still remains, said small pressure difference is, according to the invention, kept so low that the pressure difference cannot inadmissibly have an adverse effect on the flow through the chromatography column or even lead to damage to the injection valve or to the chromatography column.

The same applies analogously for the switching from the INJECT position into the LOAD position. Here, too, a switch is initially made from the INJECT position into the PRESSURE EQUALIZATION position, in which a reduction of the pressure, which corresponds substantially to the system pressure, is performed until substantially the ambient pressure is reached. Here, too, it may be the case that a small, non-problematic pressure difference remains when a switch is made from the PRESSURE EQUALIZATION position into the LOAD position.

The pressure equalization (pressure increase or pressure decrease) in the sample loop is, according to the invention, preferably realized through corresponding actuation of the drive of the sample delivery device. In this way, no disruptive fluid flows arise during the pressure equalization.

In one preferred embodiment of the invention, in the PRESSURE EQUALIZATION position of the injection valve, the two high-pressure ports are connected. In this way, the flow of the fluid through the chromatography column is maintained, and during the switching processes, no undesired peaks in the pressure profile can occur.

Said movable element in the sample delivery device may for example be in the form of a driven syringe, wherein the movable element is formed by the piston of the syringe.

It may be provided that, after the PRESSURE EQUALIZATION position of the injection valve is reached, the control unit, by a corresponding actuation of the drive, moves the piston or the movable element by a predetermined travel which suffices to generate a change in the pump volume of the sample delivery device as necessitated by elasticities of the devices which conduct the fluid and by the compressibility of the fluid itself, wherein a pressure reduction in the sample loop substantially to ambient pressure can be achieved by means of an increase in size of the pump volume, and a pressure increase in the sample loop substantially to the working pressure of the pump(s) can be achieved by means of a reduction in size of the pump volume. The movement of the movable element may be performed in controlled or regulated fashion.

To permit regulation of the pressure or final pressure during the pressure equalization in the sample loop, a pressure sensor may be provided which detects the pressure of the fluid in the closed sample loop or in the pump volume of the sample delivery device, at least during the time in which the injection valve is situated in the PRESSURE EQUALIZATION position.

In this variant, the signal of the pressure sensor is preferably supplied to the control unit, wherein the control unit compares the pressure of the fluid with a pressure setpoint value and actuates the sample delivery device such that the pressure of the fluid reaches a high pressure setpoint value before the switching of the injection valve from the PRESSURE EQUALIZATION position into the INJECT position, and/or such that the pressure of the fluid reaches a low pressure setpoint value before the switching of the injection valve from the PRESSURE EQUALIZATION position into the LOAD position.

In a further embodiment of the present invention, the sampler according to the invention preferably has a waste line which leads from the waste port into a vessel surrounding the needle seat or into the needle seat itself. According to the invention, said needle seat has a washing function. If, in the FULL PURGE position, the sample needle is moved out of the needle seat slightly, the delivered solvent can wash over the sample needle from the outside. Here, the needle seat with washing function preferably has an overflow from which the solvent can flow off into a waste vessel.

The present invention also relates to the use of a sampler according to the invention in liquid chromatography, in particular in high performance liquid chromatography. In other words, the present invention relates to a method for performing liquid chromatography using a sampler according to the invention, in particular by switching of the positions of the injection valve of the sampler according to the invention in the manner specified above. It is preferable if, during the use of the sampler according to the invention, the pump(s) for delivering the solvent/fluid are/is also used as cleaning pump(s), in particular in the PUMP PURGE position and in the FULL PURGE position.

BRIEF DESCRIPTION OF THE DRAWINGS

The invention will be discussed in more detail below on the basis of an exemplary embodiment illustrated in the drawings.

DETAILED DESCRIPTION OF THE EMBODIMENTS

Figure 1:
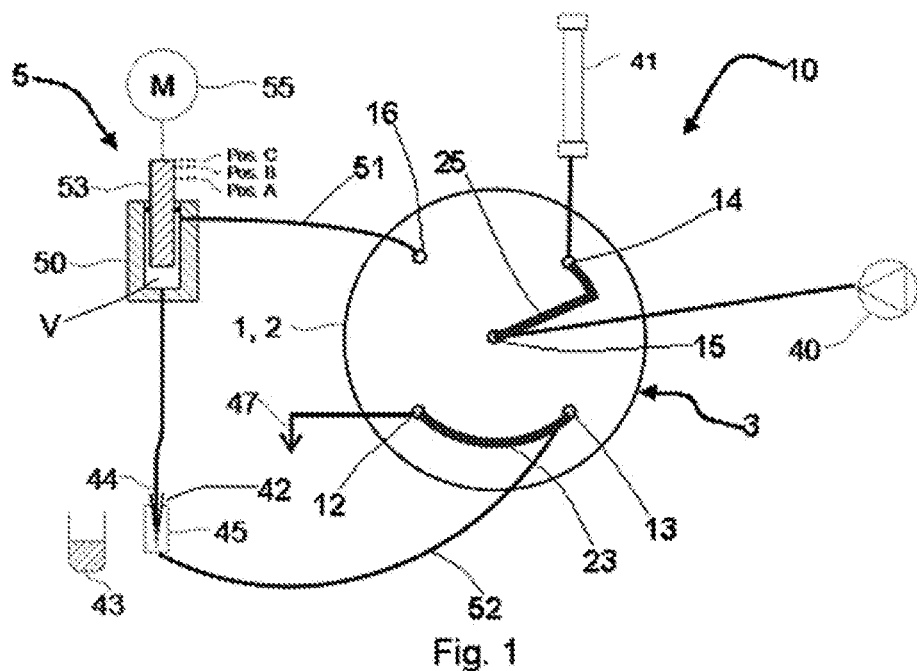
FIG. 1 is a schematic illustration of an HPLC system having a sampler according to the invention, to which a chromatography column is connected, wherein the injection valve is situated in the LOAD position.

FIG. 1 shows, in a schematic illustration, an HPLC system having a sampler 10 which operates on the basis of the split loop principle and which has a sample delivery device 5, an injection valve 3 and a pump, preferably high-pressure pump 40. Furthermore, the sampler 10 has a sample loop which is composed of the first connecting part 51 and of a second connecting part 52, 44. This may be a pressure-resistant line with a small diameter, for example in the form of glass or high-grade steel capillaries. The connecting part 51 is connected to a first sample loop port 16 of the injection valve 3 and to the sample delivery device 5, or to the pump volume V thereof. The second connecting part, which is composed of a drawing-in part 44 and a supply part 52, is designed such that it can be divided. For this purpose, the supply part 52 issues into an injection port 45 which is connected via the supply part 52 to a second sample loop port 13 of the injection valve 3. The drawing-in part 44, which at one end is connected to the pump volume V of the sample delivery device 5, has at the other end a sample needle 42 by way of which the drawing-in part 44 can be connected to the injection port 45.

Figure 4:
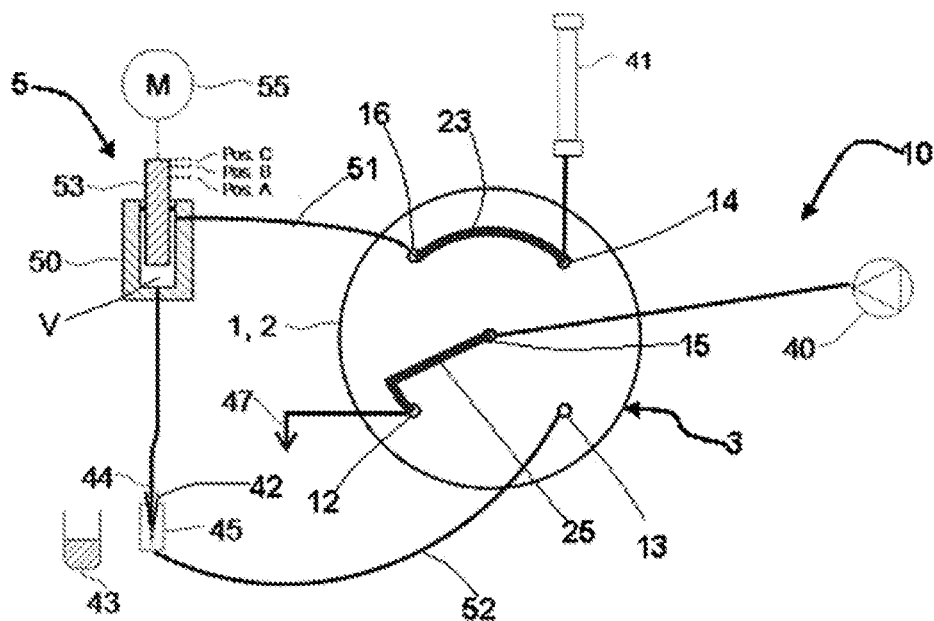
FIG. 4 shows the HPLC system from the preceding figures, wherein the injection valve has been switched into the PUMP PURGE position.

The sample needle 42 can however also be moved to a sample vessel 43 and can, in the manner discussed below, draw a defined sample volume from said sample vessel into the drawing-in part 44. Furthermore, the sample needle 42 can also be moved to a vessel for a cleaning fluid (not illustrated) in order to draw cleaning liquid from the latter into the sample delivery device 5. When the sample needle 42 is placed into the needle seat 45 again, owing to the fact that the port 13 is closed off in pressure-tight fashion (FIG. 4), it is possible, as the piston 53 is pushed downward, for the received cleaning fluid to be transported to the chromatography column via the sample loop part 51, the port 16, the groove 23 and that port 14 which is connected to the chromatography column 41. In this way, the chromatography column 41 can be cleaned. This cleaning procedure is preferably performed in the PUMP PURGE position of the injection valve, which is illustrated in FIG. 4.

In the illustrated embodiment, the sample delivery device 5 comprises a syringe 50 in which a piston 53 is guided in pressure-tight and displaceable fashion. The piston 53 is driven by means of a drive 55, for example a stepper motor. The drive is preferably actuated by a control unit (not illustrated). The control unit preferably also controls the switching processes of the injection valve 3, which has an actuable drive (not illustrated).

A waste port 12 of the injection valve is preferably connected to a waste line 47 from which a fluid can be discharged into a waste reservoir (not illustrated).

The high-pressure pump(s) 40 are/is connectable to a high-pressure port 15 of the injection valve 3. A chromatography column 41 is connectable to the further high-pressure port 14. The high-pressure pump(s) 40 may be integrated, as constituent parts, into the sampler, though may also be provided in some other unit or in a separate pump unit.

The injection valve 3 is preferably composed of a stator 1 and of a rotor 2. Here, the stator 1 preferably has the two high-pressure ports 14 and 15, the two sample loop ports 13 and 16 and the waste port 12. By way of said ports, the injection valve 3 is connected via the above-described connecting lines, which may be in the form of capillary connections, to the other functional elements of the HPLC system. The high-pressure screw connections required for this purpose are not illustrated in FIG. 1 for the sake of clarity. For simplicity, the injection valve is illustrated at the boundary surface between the stator 1 and rotor 2, wherein both the design of the face surface of the stator 1 and the design of the face surface of the rotor 2 are shown in order to facilitate understanding of the mode of operation. Within the injection valve 3, the ports are preferably in the form of bores which lead to the other side of the stator 1. In FIG. 1, the rotor 2 has the at least 2 grooves 23 and 25, which are aligned precisely with the bores of the inlet and outlet ports.

The rotor 2 is preferably pressed with a contact pressure force against the stator, such that a common interface forms between rotor 1 and stator 2, at which interface the two parts are sealed against one another. The contact pressure force is in this case configured such that the arrangement remains sealed even in the presence of the highest pressures to be expected.

In the LOAD position of the valve 3, as shown in FIG. 1, the grooves 23 and 25 are aligned with the ports 12-16 such that the groove 23 connects the sample loop port 13 to the waste port 12 and the groove 25 connects the two high-pressure ports 14 and 15. In this LOAD position, the high-pressure pump(s) 40 can thus convey fluid in the direction of the chromatography column 41. Here, the sample loop port 16 is preferably closed in pressure-tight fashion. In this LOAD position, it is furthermore possible for the sample to be taken in from a sample vessel 43. For this purpose, it is possible for the sample needle 42 to be moved into a sample vessel. There, by way of movements of the piston 53 upward, that is to say out of the sample delivery device, for example from the position A into the position C (see FIG. 1), the sample can be drawn from the sample vessel into the sample needle 42 and possibly also into the sample loop 44. Then, the sample needle 42 can be moved from the sample vessel 43 into the injection port, for the purposes of injection after pressure equalization has taken place.

In a next step, the pressure in the sample loop is brought into line with the system pressure of the chromatography column 41, that is to say with the pressure with which the high-pressure pump(s) 40 supplies/supplies fluid to the inlet of the chromatography column 41. For this purpose, the injection valve is firstly switched into a PRESSURE EQUALIZATION position in which the connecting part 51 and the second connecting part or the supply part 52 of the sample loop preferably do not have any connection to the other ports of the injection valve (FIG. 2).

Figure 3:
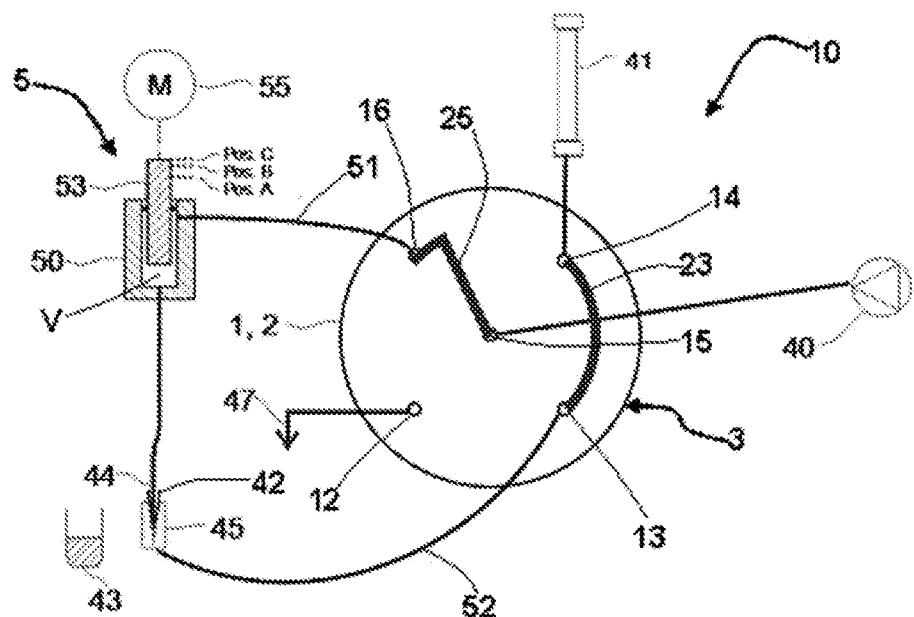
FIG. 3 shows the HPLC system from FIGS. 1 and 2, which has been switched into the INJECT position.

To adapt the pressure in the sample loop 52, 44, 51 including the sample delivery device 5 to the system pressure, it is possible for the piston 53 of the high-pressure-resistant sample delivery device 5 to be moved from the position C into position B. So as not to interrupt the flow through the chromatography column 41 during the delivery of the volume required for the compression of the sample loop content, the groove 25 in the rotor 2 is preferably of hook-shaped form such that, even in the PRESSURE EQUALIZATION position, the two high-pressure ports 14 and 15 are still connected. The delivery travel of the piston 53 from position C to position B, such as is required for the build-up of pressure, can be calculated from the compressibility of the fluid volume enclosed in the sample delivery device 5 and sample loop, from the elasticity of the arrangement, and from the present pump pressure. Alternatively, the pressure equalization may be achieved by way of a regulation loop for the pressure in the high-pressure-resistant sample delivery device. For this purpose, the pressure must be measured at a suitable location, and the position of the piston 53 in the sample delivery device 5 must be adjusted by means of the drive 55 such that the pressure corresponds to the required target pressure (=column pressure). For the pressure measurement, use may be made of a pressure sensor, or indirectly, a force measurement. A force measurement at the piston 53 or in the drive 55 are conceivable solutions. After pressure equilibrium has been achieved, the valve is switched into an INJECT position, and in this way, the drawn-in sample volume is injected into the column 41 (FIG. 3). The delivery of the sample volume to the column is preferably realized by way of the pump flow, specifically via the sample loop part 52, the sample loop port 13, the groove 23 and the high-pressure port 14.

A control unit (not illustrated) can detect the force that the drive 55 must impart in order to achieve a corresponding compression in the sample loop. For this purpose, the drive 55 may have an integrated sensor (not illustrated), the signal of which is supplied to the control unit. In this way, the control unit can determine the actual pressure in the pump volume and thus in the sample loop (the pressure drop in the connecting parts and in the valve is negligibly small) and regulate said actual pressure to the desired value.

Figure 2:
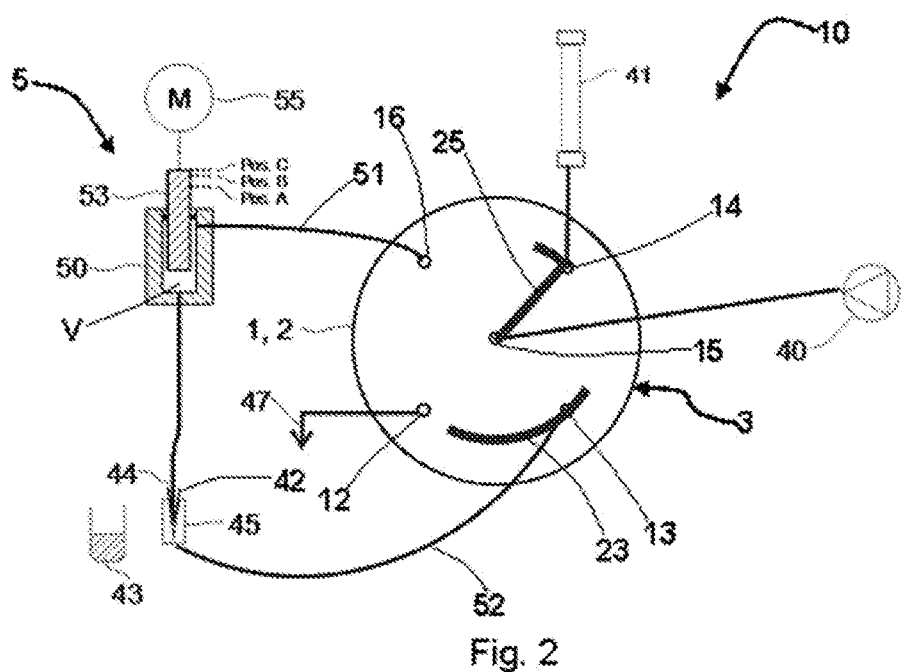
FIG. 2 shows the HPLC system in FIG. 1, wherein the injection valve has been switched from the LOAD position into the PRESSURE EQUALIZATION position.

After the drawn-in sample volume has been delivered entirely from the drawing-in part 44 to the column 41 by way of the fluid delivered by the pump(s) 40, the valve can, for the decompression of the sample loop, be switched immediately into the PRESSURE EQUALIZATION position again (FIG. 2).

Before the injection valve is moved from the PRESSURE EQUALIZATION position into the LOAD position again, the piston 53 is preferably moved into the position C. In this way, the pressure in the sample loop is brought into line with the atmospheric pressure. During this decompression time, in the PRESSURE EQUALIZATION position of the injection valve 3, the column 41 is already connected to the pump(s) 40 by way of the hook-shaped form of the groove 25 in order to avoid pressure changes. The determination of the delivery travel of the piston 53 from the position B to the position C can, as in the case of the compression, be performed mathematically or by measurement and regulation of the pressure. Alternatively, the pressure may also be determined indirectly by way of a force measurement at the piston 53 or at the drive 55 of the piston.

After the decompression of the sample loop has been performed, the valve 3 is moved into the LOAD position. Here, no damaging flows occur in the injection valve, and also, no damage is caused to the chromatography column by pressure changes. The same also applies for the compression step.

The piston 53 of the high-pressure-resistant sample delivery device 5 can now be moved into the initial position A again. The excess amount of fluid is discharged through the waste port 47. The unpressurized needle 42 can thereafter be moved from the needle seat of the injection port 45 to the corresponding sample flask in order to take in the next sample.

The position C during the decompression may also differ from the initial position C before the compression. For example, if gradients (temporally controlled mixing ratio of the solvent) are pumped through the column, said position C at the end of the decompression may be different, as the compressibility of the loop content may have changed.

The abovementioned control unit 60 may store predefined positions A, B, C and/or travel differences between said positions as a function of parameters of the sampler as a whole, in particular as a function of the compressibility of the solvent, elasticity characteristics of the sample loop and of the sample delivery device etc. Said positions can then be assumed in controlled fashion (that is to say without regulation) or may serve as approximate values or starting values for a regulated movement.

For the determination of the positions A, B, C and/or of the movement travels for the piston, a switching process of the injection valve 3 without compression or decompression may be performed. By means of a pressure sensor, it is then possible to determine the pressure drop, and to determine from this the required travel or the respective position B or C. The values thus determined may then be stored and used for further switching processes using a compression or decompression. A corresponding sensor may also be provided in the pump(s) 40. This is because such pumps for HPLC always have a pressure sensor in any case for the regulation of the delivered solvent. The compressibility of the medium, in particular of the solvent, can also be determined by means of the pump(s) 40. Such pumps are for example designed as double-piston pumps, wherein the switching from one piston to another piston is suitably controlled or regulated by means of a pressure sensor and a control unit so as to yield a highly constant flow rate. Since the compressibility of the medium must be taken into consideration for this switching process, it is possible, from the suitable actuation of the (double-piston) pump during the switch from one piston to the other, to determine the compressibility and supply this as information to the control unit.

In the case of the automatic sampler presented, it is thus ensured that in the adequately (high-)pressure-resistant sample delivery device, before the switching of the drawing-in part into the flow path to the chromatography column, that is to say before the switching of the injection valve into the INJECT position, in a special intermediate position of the injection valve, specifically the PRESSURE EQUALIZATION position, the pressure in the sample loop is brought into line with the present system pressure of the chromatography column by way of compression.

Furthermore, before the opening-up of the sample loop for the drawing-in of a sample volume from a sample vessel, that is to say before the switching of the injection valve into the LOAD position, it is preferably the case that, in the same intermediate position of the injection valve, specifically the PRESSURE EQUALIZATION position, the pressure in the sample loop is brought into line with the atmospheric pressure (decompression) through the change in volume in the sample delivery device.

FIG. 4 shows the sampler 10 according to the invention with the injection valve 3 in the PUMP PURGE position. In said position, the groove 25 connects the ports 15 and 12, such that the line from port 15 to the pump(s) 40, the groove 25 and the port 12 can be flushed with drawn-in fluid from the pump(s) 40. Here, the fluid that is flushed through, and solvent residues, are discharged from the waste line.

Figure 5:
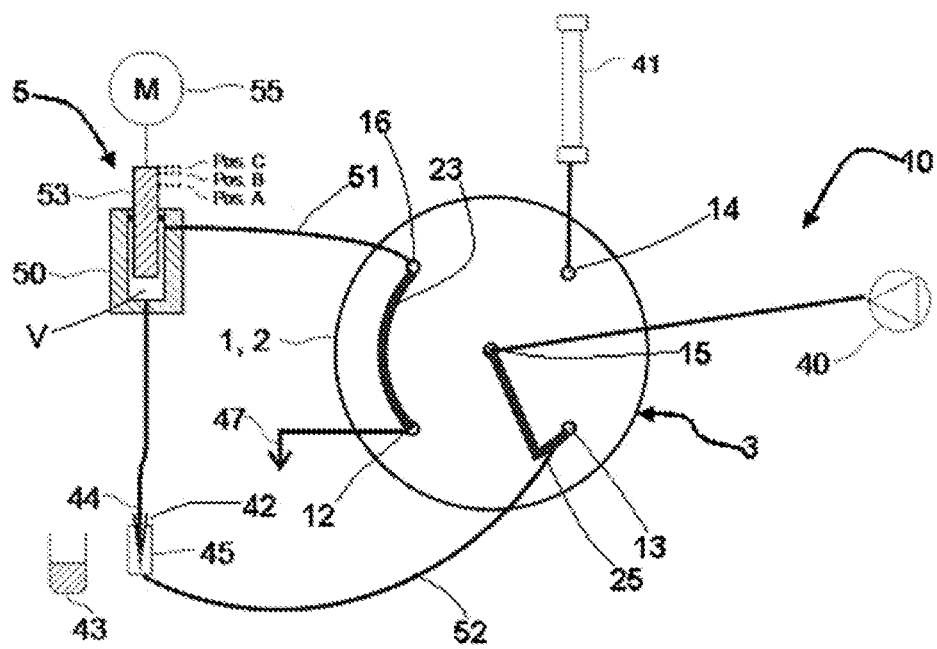
FIG. 5 shows the HPLC system from the preceding figures, wherein the injection valve has been switched into the FULL PURGE position.

FIG. 5 shows the sampler 10 according to the invention with the injection valve 3 in the FULL PURGE position. In said position, the groove 25 connects the ports 13 and 15, and the groove 23 connects the ports 16 and 12, such that the line from port 15 to the pump(s) 40, the groove 25, the port 13, the supply part 52, the sample needle 42, the needle seat 45, the drawing-in part 44, the sample delivery device 5, the sample loop part 51, the port 16, the groove 23 and the port 12 can be flushed with drawn-in fluid from the pump(s) 40. Here, the fluid that is flushed through is discharged from the waste line.

Figure 6:
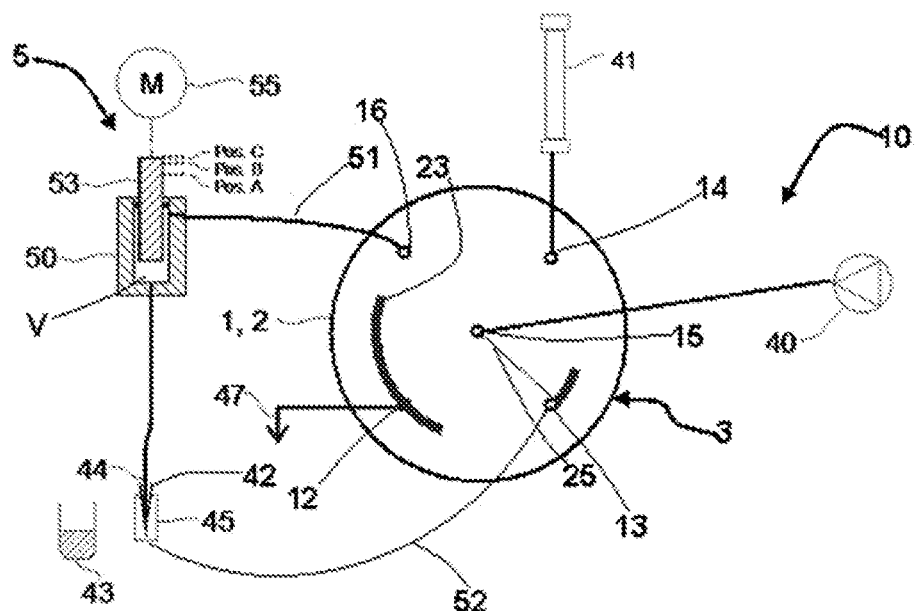
FIG. 6 shows the HPLC system from the preceding figures, wherein the injection valve has been switched into the NEGATIVE PRESSURE position.

FIG. 6 shows the sampler 10 according to the invention with the injection valve 3 in the NEGATIVE PRESSURE position. In said position, the groove 25 connects the high-pressure port 15 to the sample loop port 13. Furthermore, in said position, the sample loop port 16, the high-pressure port 14 and the waste port 12 are not connected to any other ports. The sample needle 42 is preferably situated in the needle seat 45, such that, by way of a pulling-out movement of the piston 53 of the sample delivery device 5, a negative pressure can be generated in the sample loop 51, 44, 52, in the groove 25 that connects the ports 13 and 15 to one another, and in the connecting line from port 15 to the pump(s) 40. In this way, it is possible for the hydrostatic column of the solvent to be overcome, and to assist the pump(s) 40 during the drawing-in of the solvent. Furthermore, for example before the FULL PURGE or PUMP PURGE position, gas bubbles may be removed from the device by switching into the NEGATIVE PRESSURE position and thereby generating the negative pressure. This is preferably performed while the pump(s) 40 are/is operating with delivery power lower than that produced by the negative pressure of the sample delivery device, or while the pump(s) are/is in a deactivated state.

Figure 7:
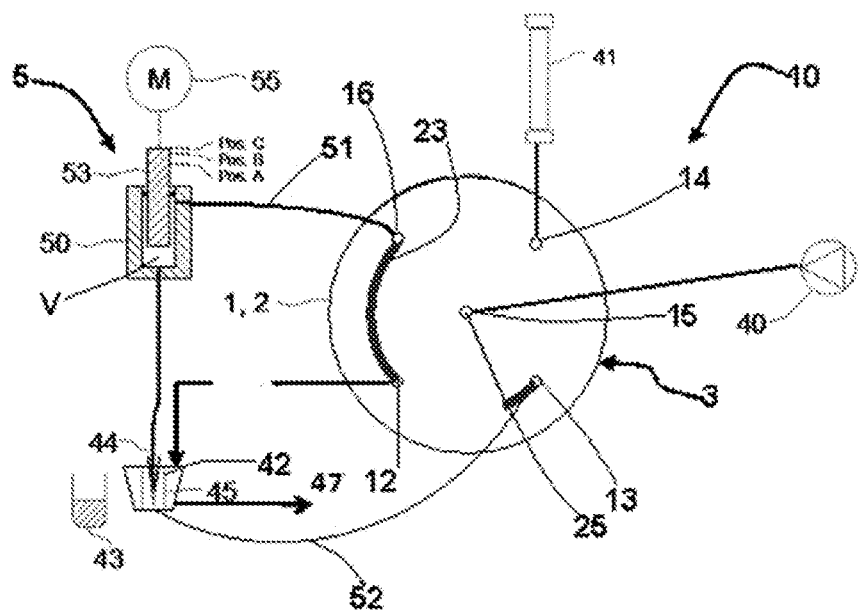
FIG. 7 shows the HPLC system from FIG. 5 in the FULL PURGE position with additional connecting line from the waste port into the wash port of the needle seat.

FIG. 7 shows a preferred embodiment according to the invention in which everything is arranged as in FIG. 5, with the only exception being that the line from the waste port 12 leads to a wash port of the needle seat, and the waste outflow 47 is situated at the wash port of the needle seat 45. In this way, during the purging in the FULL PURGE position, the cleaning agent can be conducted into the wash port of the needle seat, and thus the sample needle 42 can also be flushed from the outside. Here, the needle is preferably moved out of the needle seat slightly, such that here, the cleaning agent can already pass into the wash port of the needle seat in order to clean the outside of the sample needle, and can subsequently be discharged from the wash port into the waste.

The following reference signs are used in FIGS. 1-7.
1 Stator
2 Rotor
3 Injection valve
5 Sample delivery device
10 Sampler
12 Waste port
13 (first) sample loop port, connected to the supply part (52)
14 High-pressure port, connected to the chromatography column
15 High-pressure port, connected to the high-pressure pump
16 (second) sample loop port, connected to the sample loop part (51)
23 Arcuate groove
25 Hook-shaped groove
40 Pump(s), preferably high-pressure pump(s)
41 Chromatography column
42 Sample needle
43 Sample vessel
44 Drawing-in part
45 Injection port/needle seat
47 Waste line
50 Syringe
51 Sample loop part
52 Sample loop part or supply part
53 Movable element
55 Actuable drive
V Pump volume

What is claimed is:

1. A sampler for liquid chromatography, the sampler comprising:
   (a) an injection valve including:
      (i) at least one waste port configured to discharge fluid at a low pressure;
      (ii) a first sample loop port;
      (iii) a second sample loop port, in which the first sample loop port and the second sample loop port are both configured to supply and discharge fluid at high-pressure;
      (iv) a first high-pressure port configured to be connected to a pump;
      (v) a second high-pressure port configured to be connected to a chromatography column;
   (b) a sample loop including:
      (i) a first sample loop part, in which a first end of the first sample loop part is connected to the first sample loop port and a second end of the first sample loop part is connected to a sample delivery device; and
      (ii) a second sample loop part, in which a first end of the second sample loop part is connected to the second sample loop port and a second end of the second sample loop part is connected to the sample delivery device,
      the second sample loop part is configured to be in a divided state where the second sample loop part is divided into a drawing-in part and a supply part, in which the drawing-in part is connected to the sample delivery device, and
      in the divided state, an end of the drawing-in part is configured to draw in a sample fluid, in which the second sample loop part is also configured to be in a connected state where the drawing-in part and the supply part are connected, in the connected state, the supply part is configured to supply the sample fluid in a direction of the second sample loop port; and
   (c) the injection valve is configured to include a LOAD position and an INJECT position,
      (i) in the LOAD position, the first and second high-pressure ports are connected to one another, and the second sample loop port is connected to the waste port, and
      (ii) in the INJECT position, the first high-pressure port is connected to the first sample loop port, and the second high-pressure port is connected to the second sample loop port,
   (d) the injection valve is also configured to include additional positions, the additional positions selected from the group consisting of
      (i) a FULL PURGE position, in which the first sample loop port is connected to the waste port, and the first high-pressure port is connected to the second sample loop port,
      (ii) a PUMP PURGE position, in which the first high-pressure port is connected to the waste port,
      (iii) a NEGATIVE PRESSURE position in which the first high-pressure port is connected to the second sample loop port, and the first sample loop port is sealingly closed,
      (iv) and a combination thereof.

2. The sampler as claimed in claim 1, wherein, in the FULL PURGE position, the second high-pressure port is sealingly closed.

3. The sampler as claimed in claim 1, wherein, in the PUMP PURGE position, the second sample loop port is sealingly closed.

4. The sampler as claimed in claim 1, wherein the injection valve consists of the waste port, the first sample loop port, the second sample loop port, the first high-pressure port, and the second high-pressure port.

5. The sampler as claimed in claim 1, wherein the injection valve is also configured to include a PRESSURE EQUALIZATION position in which the first and second sample loop ports both do not have a connection to either of the first and second high-pressure ports.

6. The sampler as claimed in claim 5, wherein, in the PRESSURE EQUALIZATION position, the first and second high-pressure ports are connected to one another.

7. The sampler as claimed in claim 6, wherein the injection valve has at most six different switching positions, in which the six different switching positions consist of the LOAD position, the PRESSURE EQUALIZATION position, the INJECT position, the PUMP PURGE position, the FULL PURGE position, and the NEGATIVE PRESSURE position.

8. The sampler as claimed in claim 1, wherein the first high-pressure port is spaced apart from the first sample loop port, from the second sample loop port, from the waste port, and from the second high-pressure port by in each case a substantially same distance.

9. The sampler as claimed in claim 1, wherein the first and second sample loop ports are situated on opposite sides with respect to the first high-pressure port, and the first and second sample loop ports are both spaced apart from the waste port and from the second high-pressure port by in each case a substantially same distance.

10. The sampler as claimed in claim 1, wherein the injection valve further includes:
(vi) a rotor, and
(vii) a stator, in which a face surface of the rotor is configured to be rotated against a face surface of the stator, and in which the rotor comprises at least two grooves, in which port opening cross sections of
the first high-pressure port,
the second high-pressure port,
the first sample loop port,
the second sample loop port, and
the waste port,
are provided on the face surface of the stator and are either connected in a pressure-tight fashion or shut off in pressure-tight fashion based on a rotational position of the rotor relative to the stator.

11. The sampler as claimed in claim 10, wherein one of the at least two grooves is of an arcuate form, and another one of the at least two grooves is of a hook-shaped form.

12. The sampler as claimed in claim 11, wherein the rotor comprises at most two grooves.

13. The sampler as claimed in claim 1, wherein the sampler has a control unit configured to actuate the injection valve and the sample delivery device.

14. The sampler as claimed in claim 13, wherein the sample delivery device includes a movable element, the movable element is guided in a sealed fashion in a pump volume, in which the sampler further comprises a drive, the drive configured to move the movable element, the control unit configured to actuate the drive and deliver the sample fluid contained in the pump volume.

15. The sampler as claimed in claim 1, wherein the sample delivery device is configured to generate a pressure greater than 500 bar.

16. The sampler as claimed in claim 15, wherein the sample delivery device is configured to generate pressure greater than 1500 bar.

17. The sampler as claimed in claim 1, wherein the sample delivery device is configured to generate pressure ranging from 500 bar to 1500 bar.

18. The sampler as claimed in claim 3, wherein, in the PUMP PURGE position, the first sample loop port is connected to the second high-pressure port.

19. The sampler as claimed in claim 11, wherein the hook-shaped form is configured maintain a connection between the second high-pressure port and the first high-pressure port during a change from the LOAD position to the PRESSURE EQUALIZATION position.

20. A method of performing a liquid chromatography, the method comprising:
injecting a sample into a chromatography column using a sampler, the sampler comprising:
(a) an injection valve including:
(i) at least one waste port configured to discharge fluid at a low pressure;
(ii) a first sample loop port;
(iii) a second sample loop port, in which the first sample loop port and the second sample loop port are both configured to supply and discharge fluid at high-pressure;
(iv) a first high-pressure port configured to be connected to a pump;
(v) a second high-pressure port configured to be connected to a chromatography column;
(b) a sample loop including:
(i) a first sample loop part, in which a first end of the first sample loop part is connected to the first sample loop port and a second end of the first sample loop part is connected to a sample delivery device; and
(ii) a second sample loop part, in which a first end of the second sample loop part is connected to the second sample loop port and a second end of the second sample loop part is connected to the sample delivery device, the second sample loop part is configured to be in a divided state where the second sample loop part is divided into a drawing-in part and a supply part, in which the drawing-in part is connected to the sample delivery device, and in the divided state, an end of the drawing-in part is configured to draw in a sample fluid, in which the second sample loop part is also configured to be in a connected state where the drawing-in part and the supply part are connected, in the connected state, the supply part is configured to supply the sample fluid in a direction of the second sample loop port; and
(c) the injection valve is configured to include a LOAD position and an INJECT position,
(i) in the LOAD position, the first and second high-pressure ports are connected to one another, and the second sample loop port is connected to the second sample loop part and to the waste port, and
(ii) in the INJECT position, the first high-pressure port is connected to the first sample loop port, and the second high-pressure port is connected to the second sample loop port,
(d) the injection valve is also configured to include additional positions, the additional positions selected from the group consisting of
(i) a FULL PURGE position, in which the first sample loop port is connected to the waste port, and the first high-pressure port is connected to the second sample loop port,
(ii) a PUMP PURGE position, in which the first high-pressure port is connected to the waste port,
(ii) a NEGATIVE PRESSURE position in which the first high-pressure port is connected to the second sample loop port, and the first sample loop port is sealingly closed,
(iv) and a combination thereof.

21. A method of cleaning a sampler, the method comprising: flowing a solvent into the sampler to clean the sampler, the sampler comprising:
(a) an injection valve including:
(i) at least one waste port configured to discharge fluid at a low pressure;
(ii) a first sample loop port;
(iii) a second sample loop port, in which the first sample loop port and the second sample loop port are both configured to supply and discharge fluid at high-pressure;
(iv) a first high-pressure port configured to be connected to a pump;

(v) a second high-pressure port configured to be connected to a chromatography column;
(b) a sample loop including:
(i) a first sample loop part, in which a first end of the first sample loop part is connected to the first sample loop port and a second end of the first sample loop part is connected to a sample delivery device; and
(ii) a second sample loop part, in which a first end of the second sample loop part is connected to the second sample loop port and a second end of the second sample loop part is connected to the sample delivery device,
the second sample loop part is configured to be in a divided state where the second sample loop part is divided into a drawing-in part and a supply part, in which the drawing-in part is connected to the sample delivery device, and
in the divided state, an end of the drawing-in part is configured to draw in a sample fluid, in which the second sample loop part is also configured to be in a connected state where the drawing-in part and the supply part are connected, in the connected state, the supply part is configured to supply the sample fluid in a direction of the second sample loop port; and
(c) the injection valve is configured to include a LOAD position and an INJECT position,
(i) in the LOAD position, the first and second high-pressure ports are connected to one another, and the second sample loop port is connected to the second sample loop part and to the waste port, and
(ii) in the INJECT position, the first high-pressure port is connected to the first sample loop port, and the second high-pressure port is connected to the second sample loop port,
(d) the injection valve is also configured to include additional positions, the additional positions selected from the group consisting of
(i) a FULL PURGE position, in which the first sample loop port is connected to the waste port, and the first high-pressure port is connected to the second sample loop port,
(ii) a PUMP PURGE position, in which the first high-pressure port is connected to the waste port,
(iii) a NEGATIVE PRESSURE position in which the first high-pressure port is connected to the second sample loop port, and the first sample loop port is sealingly closed,
(iv) and a combination thereof.

22. The method of claim 21, in which a first end of the supply part is connected to the second sample loop port and a second end of the supply part is connected to a needle seat, in which the injection valve further includes: a waste line connecting the waste port to a wash port of the needle seat, the method further comprising: in the FULL PURGE position, moving the drawing-in part away from the needle seat so that the solvent washes away contaminants on an outer side of the drawing-in part and on the needle seat.

23. A sample pre-compression valve for liquid chromatography, the sample pre-compression valve comprising:
(a) a stator; and
(b) a rotor, in which a face surface of the rotor is configured to be rotated against a face surface of the stator, in which the stator comprises at least five ports, the at least five ports including a first port, a second port, a third port, a fourth port, and a fifth port, the rotor comprises at least a first groove and a second groove, in which the first groove is configured to connect to two of the at least five ports, and in which the second groove is configured to connect to a different two of the at least five ports,
(i) in a LOAD position of the sample pre-compression valve, the first groove connects the first port and the second port such that the first groove does not have a dead volume, and the second groove connects the third port and the fourth port;
(ii) in a PRESSURE EQUALIZATION position of the sample pre-compression valve, the first groove connects the first port and the second port such that the first groove does have the dead volume, and the second groove does not connect the third port and the fourth port; and
(iii) in an INJECT position of the sample pre-compression valve, the first groove connects the first port and the fifth port such that the first groove does not have the dead volume, and the second groove connects the second port and the third port.

24. The sample pre-compression valve according to claim 23, in which the stator is a circular-shaped stator, wherein the first port is arranged at a center of the circular-shaped stator and the second port is on a circular path around the center of the circular-shaped stator.

25. The sample pre-compression valve according to claim 24, wherein the third port, the fourth port, and the fifth port are arranged on the circular path around the center of the circular-shaped stator.

26. The sample pre-compression valve according to claim 23, wherein in the LOAD position and the PRESSURE EQUALIZATION position, the fifth port is not connected to the first groove, and the fifth port is not connected to the second groove.

27. The sample pre-compression valve according to claim 23, wherein in the PRESSURE EQUALIZATION position and the INJECT position, the fourth port is not connected to the first groove, and the fifth port is not connected to the second groove.

28. A method of injecting a sample into a chromatography column, the method comprising: pre-compressing a sample with a sample pre-compression valve, the sample pre-compression valve comprising:
(a) a stator; and
(b) a rotor, in which a face surface of the rotor is configured to be rotated against a face surface of the stator, in which the stator comprises at least five ports, the at least five ports including a first port, a second port, a third port, a fourth port, and a fifth port, the rotor comprises at least a first groove and a second groove, in which the first groove is configured to connect to two of the at least five ports, and in which the second groove is configured to connect to a different two of the at least five ports,
(i) in a LOAD position of the sample pre-compression valve, the first groove connects the first port and the second port such that the first groove does not have a dead volume, and the second groove connects the third port and the fourth port;
(ii) in a PRESSURE EQUALIZATION position of the sample pre-compression valve, the first groove connects the first port and the second port such that the first groove does have the dead volume, and the second groove does not connect the third port and the fourth port; and
(iii) in an INJECT position of the sample pre-compression valve, the first groove connects the first port and the fifth port such that the first groove does not have the dead volume, and the second groove connects the second port and the third port.

29. A sampler for liquid chromatography comprising:
(A) a sample pre-compression valve including:
   (a) a stator; and
   (b) a rotor, in which a face surface of the rotor is configured to be rotated against a face surface of the stator, in which the stator comprises at least five ports, the at least five ports including a first port, a second port, a third port, a fourth port, and a fifth port, the rotor comprises at least a first groove and a second groove, in which the first groove is configured to connect to two of the at least five ports, and in which the second groove is configured to connect to a different two of the at least five ports,
      (i) in a LOAD position of the sample pre-compression valve, the first groove connects the first port and the second port such that the first groove does not have a dead volume, and the second groove connects the third port and the fourth port;
      (ii) in a PRESSURE EQUALIZATION position of the sample pre-compression valve, the first groove connects the first port and the second port such that the first groove does have the dead volume, and the second groove does not connect the third port and the fourth port; and
      (iii) in an INJECT position of the sample pre-compression valve, the first groove connects the first port and the fifth port such that the first groove does not have the dead volume, and the second groove connects the second port and the third port;
(B) a sample loop connected to a sample delivery system and a needle seat;
(C) a discharge line;
(D) a solvent pump; and
(E) a chromatography column, wherein the first port is connected to the solvent pump, the second port is connected to the chromatography column, the third port is connected to the sample loop, and the fourth port is connected to the discharge line.

* * * * *

UNITED STATES PATENT AND TRADEMARK OFFICE
CERTIFICATE OF CORRECTION

PATENT NO. : 10,473,631 B2
APPLICATION NO. : 15/190529
DATED : November 12, 2019
INVENTOR(S) : Thomas Wachinger Page 1 of 1

It is certified that error appears in the above-identified patent and that said Letters Patent is hereby corrected as shown below:

In the Claims

Claim 20, Column 20, Line 3:
Replace "(ii)" with -- (iii) --

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*